(12) United States Patent
Yang et al.

(10) Patent No.: US 10,263,269 B2
(45) Date of Patent: Apr. 16, 2019

(54) CELL FOR FELT ELECTRODE CHARACTERIZATION

(71) Applicant: KOREA INSTITUTE OF ENERGY RESEARCH, Daejeon (KR)

(72) Inventors: Junghoon Yang, Daejeon (KR); Kyunam Jung, Daejeon (KR); Jaedeok Jeon, Daejeon (KR); Chanwoo Lee, Seoul (KR); Joonmok Shim, Sejong-si (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 297 days.

(21) Appl. No.: 15/216,708

(22) Filed: Jul. 22, 2016

(65) Prior Publication Data
US 2017/0059520 A1    Mar. 2, 2017

(30) Foreign Application Priority Data
Aug. 27, 2015    (KR) .......................... 10-2015-0121091

(51) Int. Cl.
| | |
|---|---|
| *G01N 27/416* | (2006.01) |
| *H01M 8/18* | (2006.01) |
| *H01M 4/86* | (2006.01) |
| *H01M 8/04* | (2016.01) |

(52) U.S. Cl.
CPC ............. *H01M 8/188* (2013.01); *H01M 4/86* (2013.01); *H01M 8/04* (2013.01); *Y02E 60/528* (2013.01)

(58) Field of Classification Search
CPC ............... H01M 8/04; H01M 8/04186; H01M 8/04194; G01N 27/4168; G01N 27/417; G01N 27/30; G01N 27/301; G01N 27/28; G01N 27/283
See application file for complete search history.

(56) References Cited

U.S. PATENT DOCUMENTS

| | | | | |
|---|---|---|---|---|
| 5,126,034 A | * | 6/1992 | Carter | .................... C12Q 1/001 |
| | | | | 204/403.05 |
| 5,578,388 A | * | 11/1996 | Faita | ......................... C25B 9/10 |
| | | | | 429/437 |

(Continued)

FOREIGN PATENT DOCUMENTS

| | | |
|---|---|---|
| JP | 2009-300388 A | 12/2009 |
| KR | 20-04638210000 Y1 | 11/2012 |

(Continued)

OTHER PUBLICATIONS

Chemours.com; What is Teflon?; archived date Feb. 14, 2016; accessed and printed Jun. 25, 2018 (Year: 2016).*

(Continued)

*Primary Examiner* — Edward J. Schmiedel
(74) *Attorney, Agent, or Firm* — Hauptman Ham, LLP (57) ABSTRACT

The present invention relates to a cell for felt electrode characterization which analyzes a characteristic of a felt electrode used in a redox flow battery. According to the present invention, the cell for felt electrode characterization can accurately analyze an electrical characteristic of the felt electrode by adjusting contact strength applied to the working electrode to be constant by adjusting the thickness of the first support that supports one side of the working electrode.

7 Claims, 10 Drawing Sheets

(56) References Cited

U.S. PATENT DOCUMENTS

| | | | | |
|---|---|---|---|---|
| 7,060,169 B2* | 6/2006 | Rohrl | ............... | C07C 211/62 |
| | | | | 204/431 |
| 2002/0153241 A1* | 10/2002 | Niv | ............... | H05H 1/2406 |
| | | | | 204/164 |

FOREIGN PATENT DOCUMENTS

| KR | 10-2015-0040638 A | 4/2015 |
|---|---|---|
| KR | 1020150095037 A | 8/2015 |

OTHER PUBLICATIONS

Korean Notice of Allowance dated Dec. 30, 2016 in connection with the counterpart Korean Patent Application No. 10-2015-0121091.

* cited by examiner

CELL FOR FELT ELECTRODE CHARACTERIZATION

CROSS-REFERENCE TO RELATED APPLICATION

This application claims priority to and the benefit of Korean Patent Application No. 10-2015-0121091 filed in the Korean Intellectual Property Office on Aug. 27, 2015, the entire contents of which are incorporated herein by reference.

BACKGROUND

1. Field of the Invention

The present invention relates to a cell for felt electrode characterization, and more particularly, to a cell for felt electrode characterization capable of analyzing a characteristic of a felt electrode which is used in a redox flow battery.

2. Discussion of Related Art

Electricity storage technology is gaining importance for efficient utilization of electricity, improved capability or reliability of an electricity supply system, introduction and expansion of renewable energy having a great variation over time, and regenerative energy of a mobile unit, that is, for an efficient use of energy throughout the energy industry, and it has an increasing growth potential and also increased expectations to make a social contribution.

Many studies on secondary batteries have been carried out in order to adjust the balance of electricity supply and demand in a semi-autonomous localized electricity supply system, such as microgrids, to properly distribute non uniform output of renewable energy generation, such as wind power generation and solar photovoltaic power generation, and to control influence on a change in voltage and frequency which is caused by a difference from an existing power system, and in these fields, more and more secondary batteries are expected to be used.

As for a secondary battery used in large-scale electricity storage, a required characteristic is a high energy storage density, and this characteristic is optimally provided by a redox flow battery that is a high capacity and high efficiency secondary battery.

A redox flow battery, different from an existing secondary battery, is a system for charging and discharging through oxidation and reduction of active material in an electrolyte, that is, an electrochemical capacitor apparatus for storing chemical energy of an electrolytic solution in the form of electric energy. The redox flow battery was first studied by the Lewis Research Centre (LRC) of the National Aeronautics and Space Administration (NASA) in 1974. The redox flow battery has been actively studied with regard to redox couples, electrochemical reaction mechanisms, ion exchange membrane development, and performance tests, and it was first sold by Sumitomo Electric Industries, Ltd. around 2000 and has been used as an electricity storage system for load leveling between day and night, voltage sag compensation, and output equalization of wind power generation.

An electrode of the redox flow battery is a conductor disposed to generate an electric field in a dielectric or obtain an electric current in a system. As a representative example of the electrode of the redox flow battery, a felt electrode is used. An electrical characteristic of the felt electrode is subject to change according to contact strength with a current collector, thus, many studies are being carried out to improve the performance of the felt electrode. However, it is difficult to accurately analyze electrical characteristics of a felt electrode.

In addition, a felt electrode is compressed in a redox flow battery manufacturing process for use, thus, it is important to predict characteristic change according to a compression ratio.

PRIOR ART DOCUMENT

Patent Document

Korean Unexamined Patent Application Publication No. 10-2015-0095037 (Aug. 20, 2015)

SUMMARY OF THE INVENTION

The present invention is directed to providing a cell for felt electrode characterization which analyzes an electrical characteristic of a felt electrode used in a redox flow battery, in which the electrical characteristic of the felt electrode is accurately analyzed by adjusting contact strength applied to the felt electrode to be constant.

One aspect of the present invention provides a cell for felt electrode characterization, the cell including: a reference electrode portion having an electrolyte chamber in which a space filled with an electrolyte is formed and a reference electrode which provides a reference value for analysis; a working electrode portion disposed at a side based on the reference electrode portion, having a working electrode which is subject to analysis, and configured to measure a response current from the working electrode while maintaining a constant pressure applied to the working electrode; and a counter electrode portion disposed at a side opposite to the working electrode portion based on the reference electrode portion, having a counter electrode, and configured to maintain charge balance according to transfer of electrons from the working electrode portion.

The working electrode or the reference electrode may include a felt electrode.

The working electrode portion may include: a first flow frame which is brought into contact with one side surface of the electrolyte chamber to receive the electrolyte, which is filling from the electrolyte chamber, and supports one side of the working electrode; an insulation film which is brought into contact with the first flow frame, and in which a receiving hole is formed at a center thereof to receive the working electrode and prevent the working electrode from moving; a first bipolar plate which is brought into contact with one side surface of the insulation film to form a closed space to prevent the electrolyte received in the first flow frame from being discharged to the outside, and supports the other side of the working electrode to fix the working electrode together with the first flow frame; and a first measurement plate which is brought into contact with one side surface of the first bipolar plate and configured to measure a current response applied from the first bipolar plate.

The first flow frame may include: a first frame in which a first opening is formed at a center thereof to receive the electrolyte; and a first support portion configured to traverse the first opening of the first frame to support one side of the working electrode, wherein the first support portion is formed with a thickness thinner than a thickness of the first frame to form a space in which the working electrode is seated.

A pressure applied to the working electrode may be determined by a depth of a step of the first support portion.

The counter electrode portion may include: a second flow frame which is brought into contact with one side surface of the electrolyte chamber, in which a second opening is formed at a center thereof to receive the electrolyte, which is filling, from the electrolyte chamber, and a second support portion which traverses the second opening to support one side of the counter electrode; a third flow frame which is brought into contact with the second flow frame, and in which a receiving hole is formed at a center thereof to receive the counter electrode to prevent the counter electrode from moving; a second bipolar plate which is brought into contact with one side surface of the third flow frame to form a closed space to prevent the electrolyte received in the second flow frame from being discharged to the outside, and supports the other side of the counter electrode to fix the counter electrode together with the second flow frame; and a second measurement plate which is brought into contact with one side surface of the second bipolar plate and configured to measure a current response applied from the second bipolar plate.

The first flow frame, the second flow frame, the third flow frame, and the insulation film may include polytetrafluoroethylene (PTFE).

The cell may further include a case configured to fix the working electrode and the counter electrode with respect to the electrolyte chamber.

The case may include: a first case disposed at a side based on the reference electrode portion to receive the working electrode portion; and a second case disposed at a side opposite to the first case based on the reference electrode portion to receive the counter electrode portion.

According to the present invention, the cell for felt electrode characterization can accurately analyze an electrical characteristic of the felt electrode by adjusting contact strength applied to the working electrode to be constant by adjusting the thickness of the first support that supports one side of the working electrode.

Accordingly, the cell for felt electrode characterization according to the present invention can accurately measure a characteristic of the felt electrode of the redox flow battery by adjusting a pressure applied to the working electrode.

DETAILED DESCRIPTION

In the following description, detailed descriptions of well-known functions or configurations will be omitted since they would obscure the invention with unnecessary detail.

It should be understood that the terms used in the specification and the appended claims should not be construed as limited to general and dictionary meanings, but should be interpreted based on the meanings and concepts corresponding to technical aspects of the present invention on the basis of the principle that the inventor is allowed to define terms appropriately for the best explanation. Therefore, the configurations shown in the drawings and the embodiments described herein are merely preferable embodiments for the purpose of illustration only and are not intended to limit the scope of the invention, so it should be understood that other equivalents and modifications could be made thereto without departing from the spirit and scope of the invention.

Hereinafter, exemplary embodiments of the present invention will be described in detail.

Figure 1:
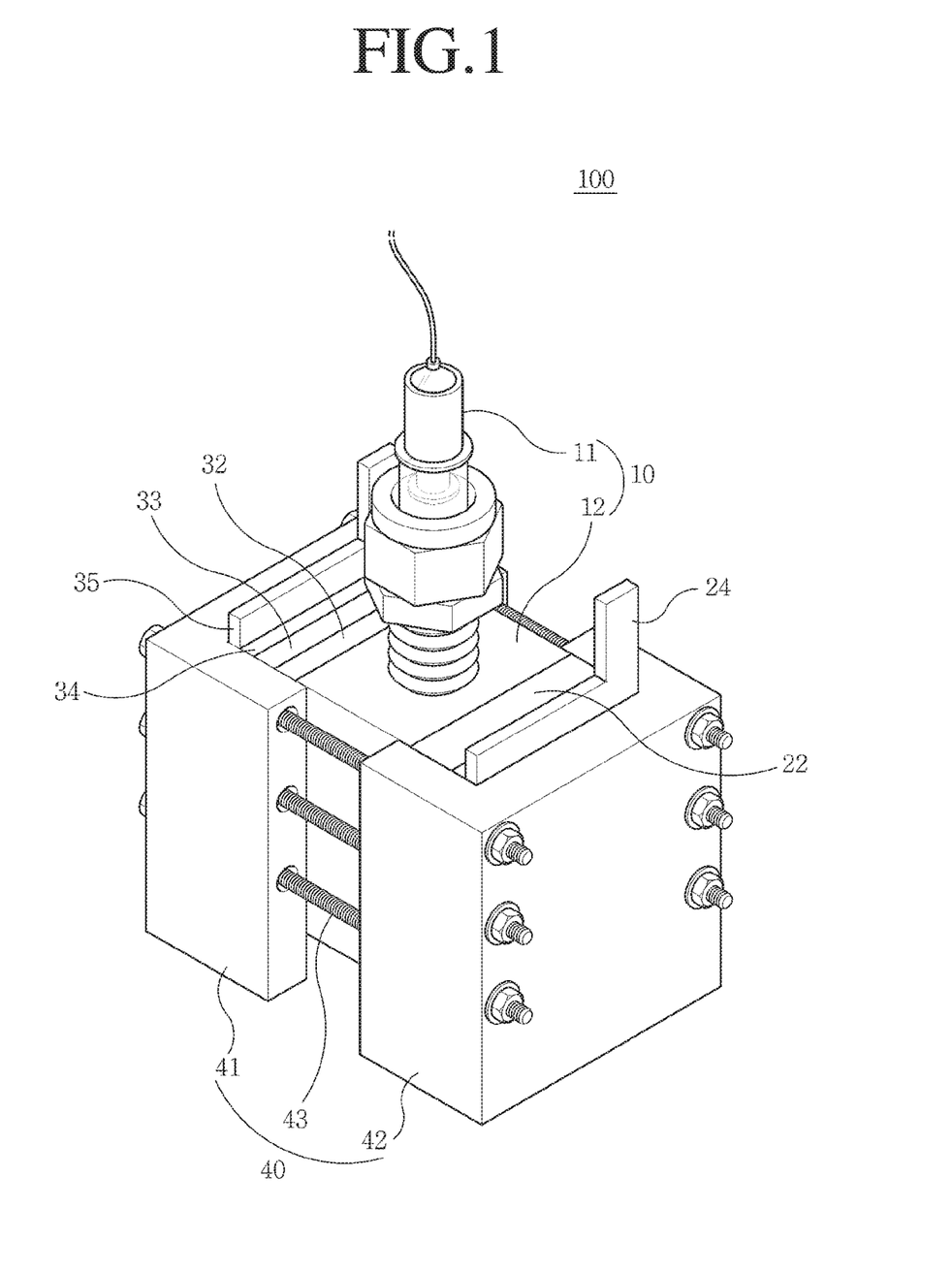
FIG. 1 is an assembled perspective view illustrating a cell for felt electrode characterization according to an embodiment of the present invention.
Figure 2:
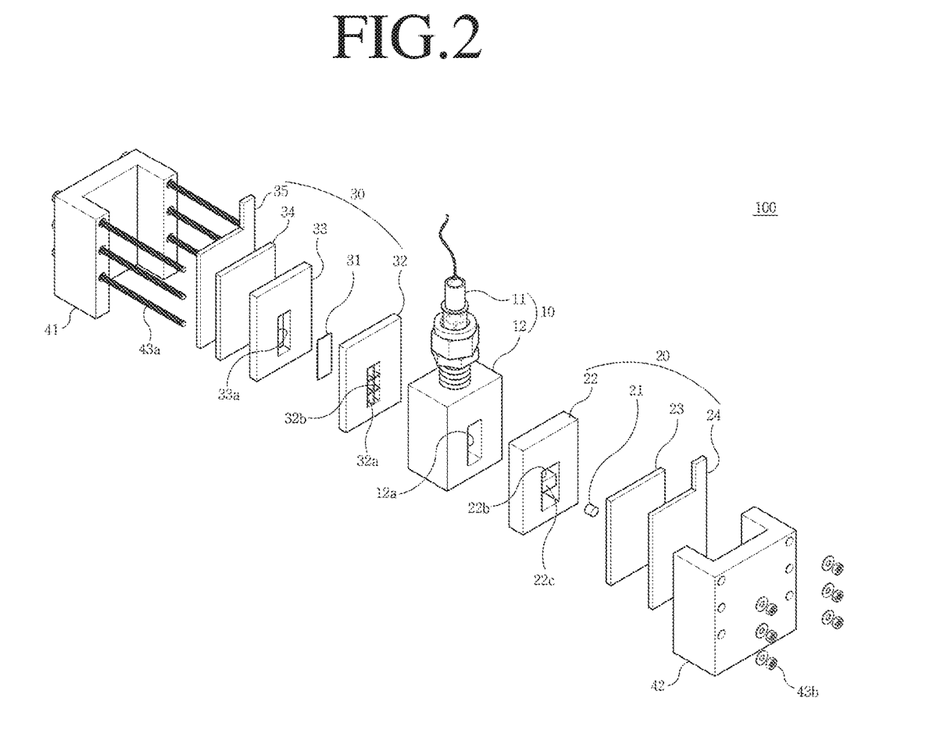
FIG. 2 is an exploded perspective view illustrating a cell for felt electrode characterization according to an embodiment of the present invention.

FIG. 1 is an assembled perspective view illustrating a cell for felt electrode characterization according to an embodiment of the present invention, and FIG. 2 is an exploded perspective view illustrating a cell for felt electrode characterization according to an embodiment of the present invention.

Referring to FIGS. 1 and 2, a cell for felt electrode characterization 100 may include a reference electrode portion 10, a working electrode portion 20, and a counter electrode portion 30, and may further include a case 40 configured to fix the working electrode portion 20 and the counter electrode portion 30 with respect to the reference electrode portion 10.

The reference electrode portion 10 is installed to accurately analyze electrical characteristics of a working electrode 21 in the cell for felt electrode characterization 100 according to an embodiment of the present invention. The reference electrode portion 10 includes a reference electrode 11 and an electrolyte chamber 12.

The electrolyte chamber 12 includes a space in which an electrolyte is filled. That is, a center portion of the electrolyte chamber 12 is perforated so as to have both sides open.

An internal space 12a of the electrolyte chamber 12, which is perforated, forms a closed space by the working electrode portion 20 and the counter electrode portion 30 to be described below, and an electrolyte fills the closed space.

The electrolyte chamber 12 has opposite side surfaces provided in a flat shape such that one side surfaces of the working electrode portion 20 and the counter electrode portion 30 come into close contact with the opposite side surfaces of the electrolyte chamber 12, respectively.

The electrolyte chamber 12 may include a through hole (not shown) passing through from an upper surface thereof to the internal space 12a. In order to accurately measure the electrical characteristics of the working electrode 21, the reference electrode 11 needs to be installed. The reference electrode 11 is inserted into the through hole by extending from the upper side of the electrolyte chamber 12 to the internal space 12a.

The reference electrode 11 is inserted to be fixed and passes through the electrolyte chamber 12 to be submergible in the electrolyte filling the internal space 12a of the electrolyte chamber 12.

The reference electrode 11 provides a reference value for a voltage applied to the working electrode 21. For example, as the reference electrode 11, a water-soluble reference electrode or an oil-soluble reference electrode may be used.

The working electrode portion 20 is disposed at one side surface based on the reference electrode portion 10, and is provided with the working electrode 21 which is subject to analysis. The working electrode portion 20 according to an embodiment of the present invention measures a response current from the working electrode 21 while maintaining a constant pressure applied to the working electrode 21.

The working electrode 21 may be a felt electrode formed of carbon, platinum, copper, aluminum, or a mixture thereof. The working electrode 21 is formed in a flat panel shape, preferably, a cylindrical shape.

The working electrode portion 20 includes a first flow frame 22, a first bipolar plate 23, and a first measurement plate 24.

The first flow frame 22 receives the electrolyte filling the electrolyte chamber 12 while making contact with one side surface of the electrolyte chamber 12, and supports one side of the working electrode 21. The first flow frame 22 may be formed of insulating material including polytetrafluoroethylene (PTFE).

The first flow frame 22 includes a first frame 22a and a first support portion 22c.

The first frame 22a may have one side surface thereof coming into contact with and fixed to the electrolyte chamber 12. In addition, the first frame 22a may be provided with a first opening 22b to receive the electrolyte at a center thereof. The first opening 22b has at least one portion thereof overlapping the internal space 12a of the electrolyte chamber 12 such that the working electrode 21 is submerged in the electrolyte filling the electrolyte chamber 12.

The first support portion 22c may be provided to traverse the first opening 22b of the first frame 22a. The first support portion 22c has a thickness thinner than a thickness of the first frame 22a to form a space in which the working electrode 21 is seated. That is, one side surface of the working electrode 21 may be supported by the first support portion 22c.

The first bipolar plate 23 may come into close contact with one side surface of the first frame 22a of the first flow frame 22 while interposing an insulation film (25 in FIG. 3) therebetween. The first bipolar plate 23 is coupled to the first frame 22a to entirely cover the first opening 22b of the first flow frame 22. Accordingly, the first bipolar plate 23 may form a closed space to prevent the electrolyte received in the first opening 22b from being discharged to the outside.

In addition, the first bipolar plate 23 may support the other side of the working electrode 21, one side of which is supported by the first support portion 22c. That is, the first bipolar plate 23 may fix the working electrode 21 together with the first support portion 22c.

The first bipolar plate 23 serves as a terminal for measuring a current or a voltage output from the working electrode 21.

The first measurement plate 24 makes contact with one side surface of the first bipolar plate 23 to measure a current or a voltage response applied from the working electrode 21 via the first bipolar plate 23.

The counter electrode portion 30 is disposed at a side opposite to the working electrode portion 20 based on the electrolyte chamber 12, has a counter electrode 31, and is configured to maintain charge balance according to transfer of electrons from the working electrode portion 20.

The counter electrode 31 may be a felt electrode formed of carbon, platinum, copper, aluminum, or a mixture thereof. The counter electrode 31 is formed in a flat panel shape, preferably, a rectangular parallelepiped shape.

Meanwhile, the working electrode 21 is an electrode which is subject to electrical characteristic analysis, thus, a reaction at the working electrode 21 needs to be prevented from being affected by the counter electrode 31. The counter electrode 31 serves to aid in flowing electric current. Therefore, the counter electrode 31 is manufactured to have a cross section at least several ten-fold greater than a cross section of the working electrode 21. For example, the counter electrode 31 may have a cross section at least ten-fold greater than a cross section of the working electrode 21. The counter electrode 31 having a cross section smaller than the above may cause errors in information collected from analyzing electrical characteristic of the working electrode 21.

The counter electrode portion 30 includes a second flow frame 32, a third flow frame 33, a second bipolar plate 34, and a second measurement plate 35.

The second flow frame 32 receives the electrolyte filling the electrolyte chamber 12 while making contact with one side surface of the electrolyte chamber 12, and supports one side of the counter electrode 31. The second flow frame 32 may be formed of insulating material including polytetrafluoroethylene (PTFE).

The second flow frame 32 may be provided with a second opening 32a to receive the filling electrolyte from the electrolyte chamber 12 at a center thereof.

The second opening 32a has at least one portion thereof overlapping the internal space 12a of the electrolyte chamber 12 such that the counter electrode 31 is submerged in the electrolyte filling the electrolyte chamber 12.

In addition, the second flow frame 32 may include a second support portion 32b traversing the second opening 32a to support one side of the counter electrode 31.

The second support portion 32b may be provided in an arrangement of a plurality of bars that traverse the second opening 32a to support the counter electrode 31 which has an area larger than that of the working electrode 21.

The third flow frame 33 may make contact with the second flow frame 32. A center of the third flow frame 33 may be provided with a receiving hole 33a which is configured to receive the counter electrode 31 to prevent the counter electrode 31 from moving. The third flow frame 33 may be formed of insulating material including polytetrafluoroethylene (PTFE).

The second bipolar plate 34 may make close contact with one side surface of the third flow frame 33. The second bipolar plate 34 is coupled to the third flow frame 33 to entirely cover the receiving hole 33a of the third flow frame 33. Accordingly, the second bipolar plate 34 may form a closed space, the closed space configured to prevent the electrolyte received in the receiving hole 33a and the second opening 32a of the second flow frame 32 from being discharged to the outside.

In addition, the second bipolar plate 34 supports the other side of the counter electrode 31, one side of which is supported by the second support portion 32b. That is, the second bipolar plate 34 may fix the counter electrode 31 together with the second support portion 32b.

The second bipolar plate 34 serves as a terminal for measuring a current or a voltage output from the counter electrode 31.

The second measurement plate 35 makes contact with one side surface of the second bipolar plate 34 to measure a current or a voltage response applied from the counter electrode 31 via the second bipolar plate 34.

Meanwhile, the case 40 may fix the working electrode portion 20 and the counter electrode portion 30 with respect to the electrolyte chamber 12. The case 40 may include a first case 41, a second case 42, and a connecting member 43.

The first case 41 may be provided with a receiving space to receive the counter electrode portion 30. The receiving space of the first case 41 may have an area larger than a cross section of each component of the counter electrode portion 30, that is, the second flow frame 32, the third flow frame 33, the second bipolar plate 34, and the second measurement plate 35 while preventing each component of the counter electrode portion 30 from moving. Although not shown, a lower side of the first case 41 is provided with a holding step (not shown) on which each component of the counter electrode portion 30 is seated without being released.

The second case 42 may be provided with a receiving space to receive the working electrode portion 20. The receiving space of the second case 42 may have an area larger than a cross section of each component of the working electrode portion 20, while preventing each component of the working electrode portion 20 from moving. A lower side of the second case 42 is provided with a holding step (not shown) on which each component of the working electrode portion 20 is seated without being released.

The first case 41 and the second case 42 are connected to and fixed to each other by the connecting member 43 with respect to the electrolyte chamber 12. The connecting member 43 includes a bolt 43a and a nut 43b to fix the first case 41 and the second case 42. That is, the bolt 43a of the connecting member 43 connects the first case 41 to the second case 42 by passing through the first and second cases 41 and 42, and the first and second cases 41 and 42 are fastened by the nut 43b, thereby fixing the working electrode portion 20 and the counter electrode portion 30 seated in the first case 41 and the second case 42 with respect to the reference electrode portion 10.

Hereinafter, the working electrode portion 20 of the cell for felt electrode characterization will be described in more detail with reference to the accompanying drawings.

Figure 3:
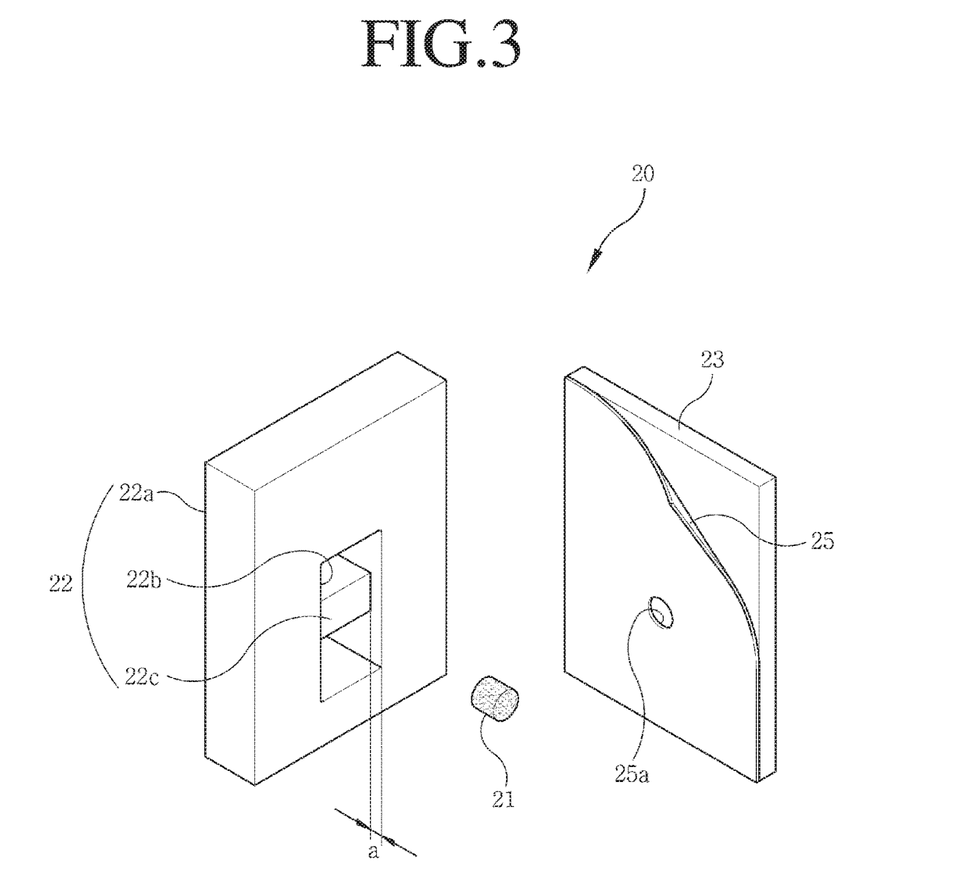
FIG. 3 is a view illustrating a working electrode portion of a cell for felt electrode characterization according to an embodiment of the present invention.

FIG. 3 is a view illustrating the working electrode portion 20 of a cell for felt electrode characterization according to an embodiment of the present invention.

Referring to FIGS. 2 and 3, the working electrode portion 20 includes the first flow frame 22, the insulation film 25, the first bipolar plate 23, and the first measurement plate 24 as described above.

In particular, the cell for felt electrode characterization 100 according to an embodiment of the present invention may adjust a pressure applied to the working electrode 21 by using the first flow frame 22.

The first support portion 22c of the first flow frame 22 is formed with a thickness thinner than that of the first frame 22a so that a space in which the working electrode 21 is seated may be formed. That is, as the first support portion 22c is formed with a thickness thinner than that of the first frame 22a, a step (a) is generated between the first support portion 22c and the first frame 22a. The working electrode 21 is disposed in a space defined by the step (a) between the first support portion 22c and the first frame 22a.

Accordingly, a pressure applied to the working electrode 21 may be determined by the depth of the step of the first support portion 22c.

In this manner, the cell for felt electrode characterization 100 according to an embodiment of the present invention may adjust a contact strength applied to the working electrode 21 to be constant by adjusting the thickness of the first support portion 22c that supports one side of the working electrode 21, so that the electrical characteristics of the felt electrode can be accurately analyzed.

In addition, a center of the insulation film 25 may be provided with a receiving hole 25a to receive the working electrode 21. Accordingly, the insulation film 25 may prevent the working electrode 21 from moving by use of the receiving hole 25a. The insulation film 25 may be formed of insulating material including polytetrafluoroethylene (PTFE).

Accordingly, the insulation film 25 may allow the working electrode 21 to make contact with the first bipolar plate 23 through the receiving hole 25a while exposing only a portion of the working electrode 21 to the electrolyte, so that the electrical characteristic analysis of the working electrode 21 can be more accurately performed.

The following description compares the cell for felt electrode characterization 100 according to an embodiment of the present invention with a cell for felt electrode characterization 200 according to a first comparative example and a cell for electrode characterization 300 according to a second comparative example.

Figure 4:
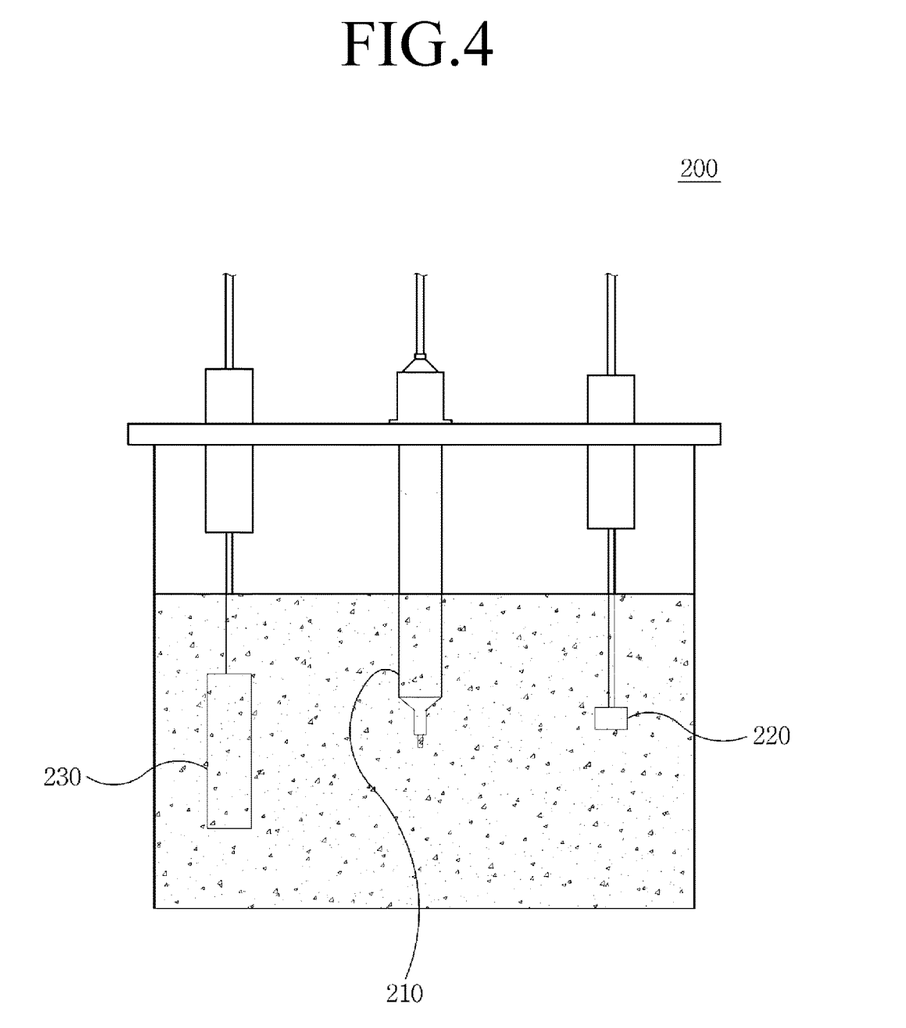
FIG. 4 is a view illustrating a configuration of a cell for felt electrode characterization according to a first comparative example.
Figure 5:
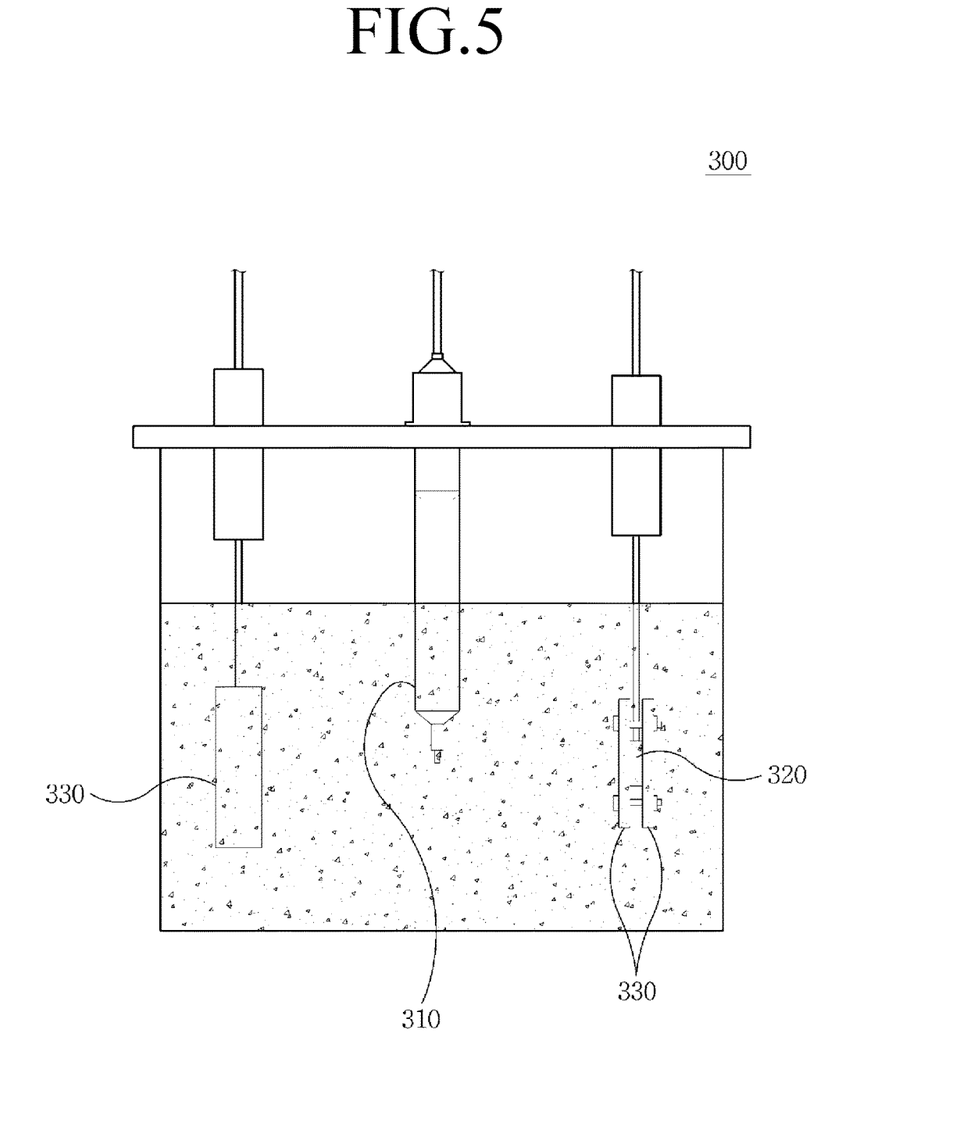
FIG. 5 is a view illustrating a configuration of a cell for felt electrode characterization according to a second comparative example.

FIG. 4 is a view illustrating a configuration of a cell for felt electrode characterization according to the first comparative example, and FIG. 5 is a view illustrating a configuration of a cell for felt electrode characterization according to the second comparative example First Comparative Example Referring to FIG. 4, the cell for felt electrode characterization 200 according to the first comparative example includes a container filled with an electrolyte and a reference electrode 210, a working electrode 220, and a counter electrode 230 that are submerged in the electrolyte.

Second Comparative Example

Referring to FIG. 5, the cell for felt electrode characterization 300 according to the second comparative example includes a container filled with an electrolyte and a reference electrode 310, a working electrode 320, and a counter electrode 330 that are submerged in the electrolyte.

The cell for felt electrode characterization 300 according to the second comparative example may further include a compression plate 340 to compress the working electrode 320 such that a constant pressure is applied to the working electrode 320.

The cell for felt electrode characterization 100 according to an embodiment of the present invention, the cell for felt electrode characterization 200 according to the first comparative example, and the cell for felt electrode characterization 300 according to the second comparative example are repeatedly analyzed through cyclic voltammetry.

Figure 6:
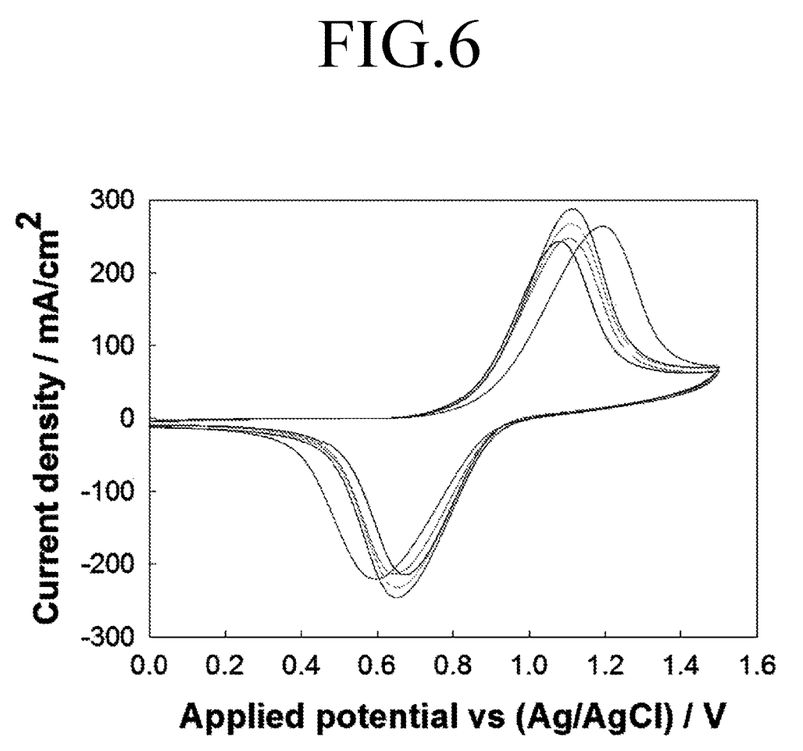
FIG. 6 is a graph showing a current response characteristic of a working electrode that is analyzed using a cell for felt electrode characterization according to a first comparative example.

FIG. 6 is a graph showing a current response characteristic of a working electrode that is analyzed using the cell for felt electrode characterization 200 according to the first comparative example.

Referring to FIG. 6, in the case of performing a repeated analysis using the cell for felt electrode characterization 200 according to the first comparative example, it can be seen that analysis results are not uniform and a deviation occurs at each result value.

Figure 7:
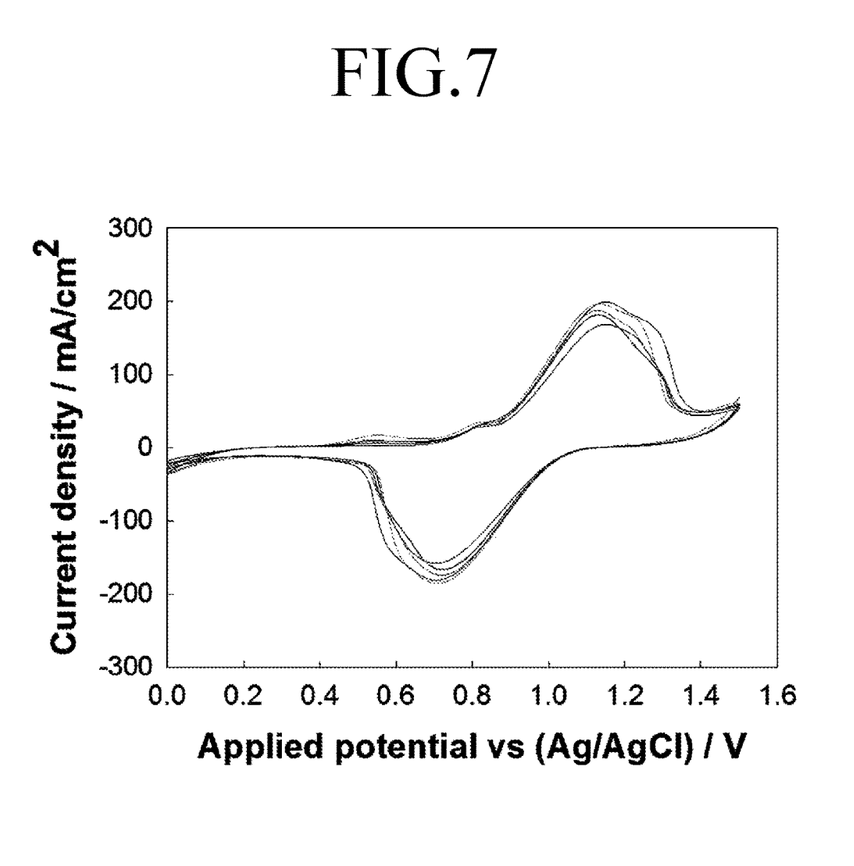
FIG. 7 is a graph showing a current response characteristic of a working electrode that is analyzed using a cell for felt electrode characterization according to a second comparative example.

Meanwhile, FIG. 7 is a graph showing a current response characteristic of a working electrode that is analyzed using a cell for felt electrode characterization 300 according to the second comparative example.

Referring to FIG. 7, in the case of performing a repeated analysis using the cell for felt electrode characterization 300 according to the second comparative example, analysis results show a superior reproducibility compared to the cell for felt electrode characterization 200 according to the first comparative example, but it can be seen that they are not uniform and a deviation occurs at each result value.

Figure 8:
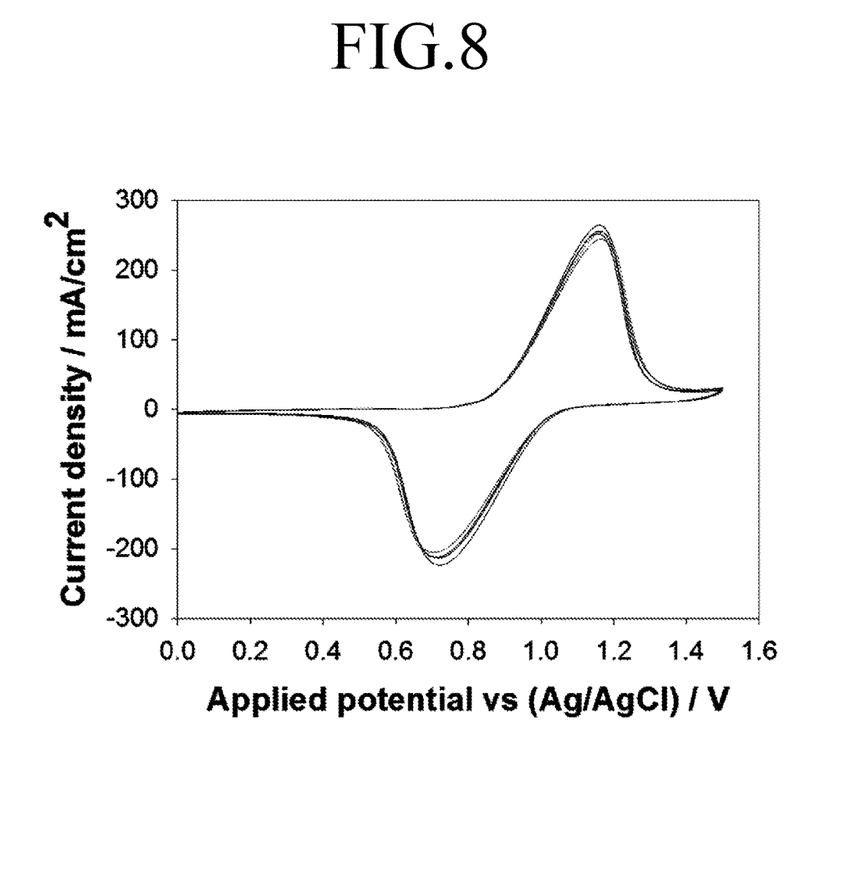
FIG. 8 is a graph showing a current response characteristic of a working electrode that is analyzed using a cell for felt electrode characterization according to an embodiment of the present invention.

FIG. 8 is a graph showing a current response characteristic of a working electrode that is analyzed using a cell for felt electrode characterization according to an embodiment of the present invention.

Referring to FIG. 8, in the case of performing a repeated analysis using the cell for felt electrode characterization 100 according to an embodiment of the present invention, analysis results have nearly no deviation occurring at a result value compared to the first and second comparative examples.

Figure 9:
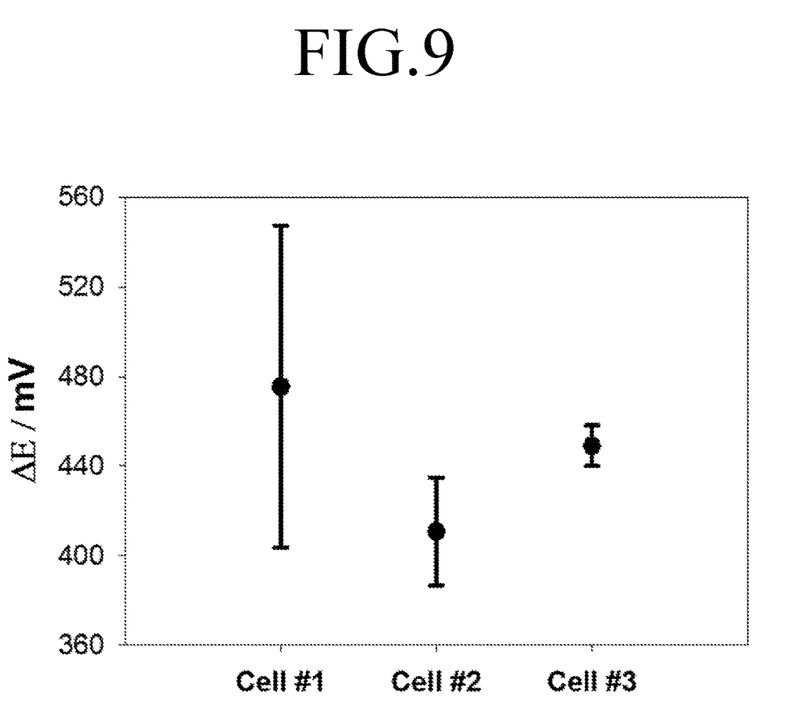
FIG. 9 is a graph showing difference among x-coordinate variation values at peaks of FIGS. 6 to 8.

FIG. 9 is a graph showing difference between x-coordinate variation values at peaks of FIGS. 6 to 8, and FIG. 10 is a graph showing current density values at anodic peaks of FIGS. 6 to 8.

Figure 10:
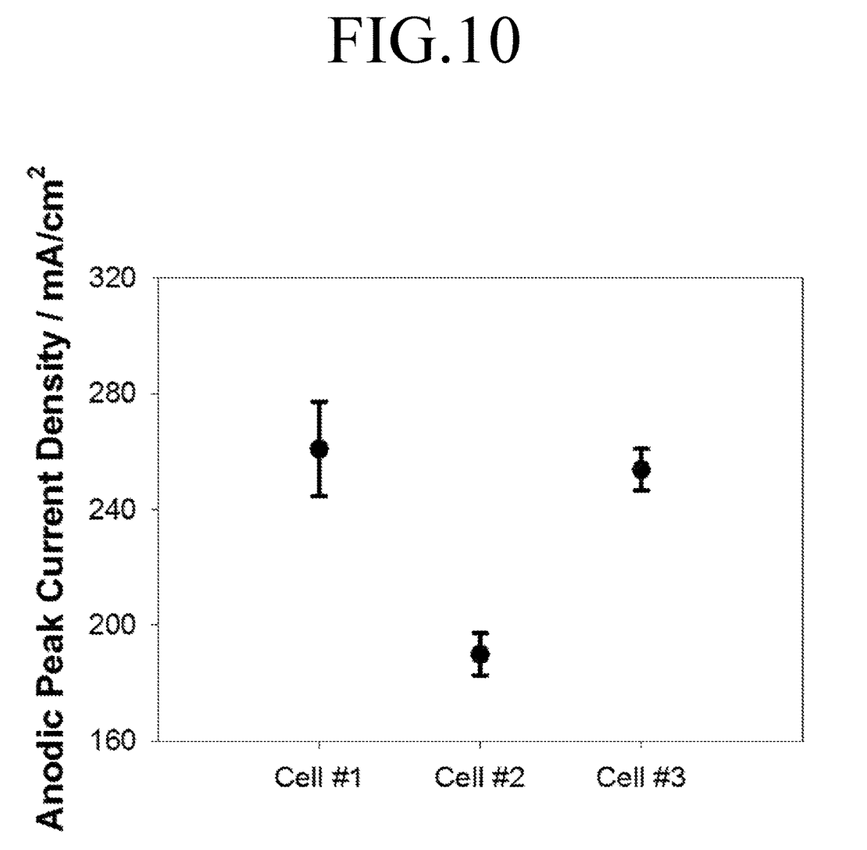
FIG. 10 is a graph showing current density values at anodic peaks of FIGS. 6 to 8.

Referring to FIGS. 9 and 10, it can be seen that results of the repeated analysis of the cell for felt electrode characterization 100 show that an x-coordinate variation value at a peak and a current density value at an anodic peak have errors significantly lower than those of results in the first comparative example and the second comparative example. As such, it was confirmed that the cell for felt electrode characterization 100 according to an embodiment of the present invention has a superior reproducibility compared to the first and second comparative examples.

The foregoing is intended merely to aid in the understanding of the background of the present invention, and is not intended to limit the scope of the present invention. Those skilled in the art will appreciate that various modifications, changes and substitutions are possible, without departing from the scope and spirit of the invention.

What is claimed is:

1. A cell for felt electrode characterization, the cell comprising:
    a reference electrode portion having
        an electrolyte chamber in which a space filled with an electrolyte is formed and having a top surface, a first side surface, and a second side surface opposite to the first side surface, and
        a reference electrode disposed at the top surface of the electrolyte chamber and configured to provide a reference value;
    a working electrode portion disposed at the first side surface of the electrolyte chamber and having a working electrode provided as a felt electrode, and configured to receive a first current from the working electrode; and
    a counter electrode portion disposed at the second side surface of the electrolyte chamber and having a counter electrode, and configured to maintain charge balance according to transfer of electrons from the working electrode portion,
    wherein the working electrode portion comprises:
        a first flow frame contacted with the first side surface of the electrolyte chamber and having a first opening to receive the electrolyte from electrolyte chamber;
        an insulation film contacted with the first flow frame and having a first receiving hole formed at a center thereof to receive the working electrode;
        a first bipolar plate contacted with the insulation film and the working electrode so as to form a first closed space by the first opening and the first receiving hole, wherein the first closed space prevents the electrolyte received in the first opening from being discharged to outside the cell; and
        a first measurement plate contacted with the first bipolar plate and configured to receive the first current applied from the working electrode via the first bipolar plate,
    wherein the first measurement plate, the first bipolar plate, the insulation film, and the first flow frame are sequentially disposed from the first measurement plate,
    wherein the counter electrode portion comprises:
        a second flow frame contacted with the second side surface of the electrolyte chamber and having a second opening to receive the electrolyte from electrolyte chamber;
        a third flow frame contacted with the second flow frame and having a second receiving hole formed at a center thereof to receive the counter electrode;
        a second bipolar plate contacted with the third flow frame and the counter electrode so as to form a second closed space by the second opening and the second receiving hole, wherein the second closed space prevents the electrolyte received in the second receiving hole of the third flow frame and the second opening of the second flow frame from being discharged to outside the cell; and
        a second measurement plate contacted with the second bipolar plate and configured to receive a second current applied from the counter electrode via the second bipolar plate,
    wherein the second measurement plate, the second bipolar plate, the third flow frame, and the second flow frame are sequentially disposed from the second measurement plate.

2. The cell of claim 1,
    wherein the first flow frame comprises a first support portion formed across the first opening to be contacted with the working electrode, and
    wherein the first support portion is formed with a thickness thinner than a thickness of a rest of the first frame to form a space in which the working electrode is seated.

3. The cell of claim 2, wherein a pressure applied to the working electrode is determined by a depth of a step of the first support portion.

4. The cell of claim 1,
    wherein the second flow frame comprises a second support portion formed across the second opening to be contacted with the counter electrode.

5. The cell of claim 4, wherein the first flow frame, the second flow frame, the third flow frame, and the insulation film include polytetrafluoroethylene (PTFE).

6. The cell of claim 1, further comprising
a case coupled to the working electrode portion and the counter electrode with the electrolyte chamber therebetween.

7. The cell of claim 6, wherein the case comprises:
a first case coupled to the working electrode portion;
a second case coupled to the counter electrode portion; and
a fixing member coupled to the first case and the second case with the electrolyte chamber therebetween.

* * * * *